(12) United States Patent
Tauber (10) Patent No.: US 8,518,119 B2
(45) Date of Patent: Aug. 27, 2013

(54) BONE FIXATION SURFACES FOR INTERVERTEBRAL IMPLANTS (75) Inventor: Michael Tauber, Haifa (IL)

(73) Assignee: Faneuil Innovation Investments Ltd., Charlestown, Saint Kitts and Nevis ( * ) Notice: Subject to any disclaimer, the term of this patent is extended or adjusted under 35 U.S.C. 154(b) by 532 days.

(21) Appl. No.: 12/526,782

(22) PCT Filed: Aug. 23, 2007

(86) PCT No.: PCT/IL2007/001052
§ 371 (c)(1),
(2), (4) Date: Aug. 12, 2009

(87) PCT Pub. No.: WO2008/102333
PCT Pub. Date: Aug. 28, 2008

(65) Prior Publication Data
US 2010/0042220 A1 Feb. 18, 2010

(51) Int. Cl.
A61F 2/44 (2006.01)

(52) U.S. Cl.
USPC ............ 623/17.16; 623/17.12; 623/17.13; 623/17.14; 623/17.15

(58) Field of Classification Search
USPC ............................ 623/17.11–17.16
See application file for complete search history.

(56) References Cited

U.S. PATENT DOCUMENTS

| | | | |
|---|---|---|---|
| 5,425,773 A | 6/1995 | Boyd | |
| 5,562,738 A | 10/1996 | Boyd | |
| 6,423,095 B1 * | 7/2002 | Van Hoeck et al. | 623/17.16 |
| 6,989,032 B2 | 1/2006 | Errico et al. | |
| 6,994,727 B2 | 2/2006 | Khandkar et al. | |
| 7,048,766 B2 | 5/2006 | Ferree et al. | |
| 7,083,649 B2 | 8/2006 | Zucherman et al. | |
| 7,291,173 B2 | 11/2007 | Richelsoph | |
| 7,806,933 B2 | 10/2010 | Sears | |
| 8,038,713 B2 | 10/2011 | Ferree | |
| 2004/0034426 A1 * | 2/2004 | Errico et al. | 623/17.13 |
| 2004/0267364 A1 * | 12/2004 | Carli et al. | 623/17.14 |
| 2008/0154378 A1 * | 6/2008 | Pelo | 623/17.16 |

* cited by examiner

Primary Examiner — Michael T Schaper
(74) Attorney, Agent, or Firm — Mark M. Friedman (57) ABSTRACT An intervertebral implant has an implant structure providing a fixation surface for fixation to the endplate of a vertebral body. The fixation surface includes two bone contact regions at different heights in an axial direction. A transition between the two contact regions has a stepped form including at least two steps.

16 Claims, 12 Drawing Sheets

BONE FIXATION SURFACES FOR INTERVERTEBRAL IMPLANTS

RELATED APPLICATIONS

This patent application is a National Stage of PCT/IL07/001052 filed on Aug. 23, 2007, which claims the benefit of PCT/IL07/000239 filed on Feb. 22, 2007,which claims the benefit of U.S. Provisional Patent Application No. 60/775,772 filed Feb. 23, 2006, the contents of which are incorporated herein by reference.

FIELD AND BACKGROUND OF THE INVENTION

The present invention relates to fixation of intervertebral implants and, in particular, it concerns intervertebral disc replacements or spacers which have stepped endplate surfaces to provide stable load support via cortical and endplate tissues combined with prompt fixation to promote the desired osteointegration.

Intervertebral implants such as total disc replacements ("TDR") and intervertebral spacers (or "cages") must be firmly fixed to the vertebral endplates immediately after implantation. Post-operative migration of intervertebral implants is a serious complication. Such migration may occur into cancellous bone core of the vertebral body ("subsidence"), and/or to any direction outside to the intervertebral space, damaging the vertebral body and disrupting the vertebral alignment. Implant migration also carries with it a high risk of both functional failure and damage to the nervous and/or visceral structures. Migration of an artificial disc may require either removal of the disc or disc maintenance, both followed by fusion, or re-implantation or repositioning of a TDR. Other risks include facet joints disruption. Thus, permanent prompt stable fixation of the implant is crucial in order for implants to withstand the compressive, shear and torque forces occurring within the intervertebral space.

Various attempts have been made to develop intervertebral implants which achieve both immediate fixation and long-term post-implantation stability. Approaches commonly used in existing intervertebral implants typically try to achieve effective fixation by increasing the contact area or "footprint" of the device, and by employing auxiliary fixation elements such as pins, nails, or screws, or by addition of vertical ribs or keels on the contact surfaces themselves. Despite expectations that the penetration of these auxiliary elements into the vertebral body should provide firm fixation, the results have not proven to be consistent. Furthermore, the perforation of sharp anchoring elements into the vertebral body carries with it the risk of vertebral body fracture and/or failure to osteointegrate.

A further problem hampering stable intervertebral implant fixation is the need to restore the natural arch of the spinal column known as lordosis. In order to reproduce this natural curvature, an intervertebral implant should provide an angle of inclination between the upper and lower fixation surfaces. However, such an angle of inclination generates a wedge-like overall profile which, when combined with normal axial loading of the vertebral column, may contribute to migration of the implant.

Some examples of intervertebral implants illustrating various approaches to fixation may be found in the following US patents and published applications nos.: U.S. Pat. Nos. 5,425,773; 6,989,032; 6,994,727; 7,048,766; 2004/0073311; and 2004/0225364.

There is therefore a need for an intervertebral implant with a tiered endplate surface to provide stable load support via cortical tissue combined with a desired degree of lordosis. It would also be advantageous to provide an intervertebral implant which would employ a combination of non-sharp features to provide prompt fixation to promote osteointegration and to provide structural support primarily through the structurally strong cortical bone tissue of the vertebrae.

SUMMARY OF THE INVENTION

The present invention is an intervertebral implant with a stepped endplate surface to provide stable load support via cortical and endplate tissues combined with prompt fixation to promote the desired osteointegration.

Thus, according to the teachings of the present invention, there is provided an intervertebral implant for deployment between an inferior endplate of a superior vertebral body and a superior endplate of an inferior vertebral body of a spinal column, the implant comprising an implant structure including at least one implant element, the implant structure providing a first fixation surface for fixation to one of the vertebral endplates, the first fixation surface including a first bone contact region and a second bone contact region, the second bone contact region being higher in an axial direction than the first bone contact region, wherein a transition from the first bone contact region to the second bone contact region has a stepped form including at least two steps.

According to a further feature of the present invention, According to a further feature of the present invention, adjacent steps of the at least two steps are spaced apart by between 5 percent and 40 percent, and preferably between 7 percent and 15 percent, of a posterior-anterior dimension of the first fixation surface.

According to a further feature of the present invention, a height of each of the at least two steps is less than a width of contact surfaces on both sides of the step.

According to a further feature of the present invention, the stepped form further includes at least one projecting ridge extending along, and adjacent to, at least part of a length of one of the steps.

According to a further feature of the present invention, the at least one projecting ridge has a flank surface which runs into one of the steps.

According to a further feature of the present invention, the at least one projecting ridge terminates at end surfaces deployed to inhibit migration of the implant parallel to the steps.

According to a further feature of the present invention, the stepped form is located at least in part in a primary load-bearing region extending at least around a major part of a periphery of the first fixation surface.

According to a further feature of the present invention, the primary load-bearing region exhibits: (a) a generally concave form in a lateral-lateral direction; and (b) the stepped form in an anterior-posterior direction, wherein upper contact surfaces of each of the steps are arranged to provide non-migratory support against loading in a primary load-bearing direction, the stepped form defining an effective lordosis plane inclined relative to the primary load-bearing direction.

According to a further feature of the present invention, the primary load-bearing region extends inwards at least about 2 millimeters from the periphery of the first fixation surface.

According to a further feature of the present invention, the primary load-bearing region extends over substantially the entirety of the first fixation surface.

According to a further feature of the present invention, the first fixation surface further features at least one press-fit anchoring projection, the press-fit anchoring projection having an axial dimension smaller than both its anterior-posterior and its lateral-lateral dimensions, and being formed with at least two opposing faces inclined to provide a wedge angle of between 1 degree and 30 degrees.

According to a further feature of the present invention, the press-fit anchoring projection is formed with corner regions deployed to provide anchoring against axial rotational migration of the intervertebral implant.

According to a further feature of the present invention, the first fixation surface further includes a convex central region.

According to a further feature of the present invention, at least part of the convex central region has a stepped form.

According to a further feature of the present invention, the convex central region further includes a plurality of non-sharp ridges extending along edges of steps of the stepped form.

According to a further feature of the present invention, the implant structure further provides a second fixation surface for fixation to the other of the vertebral endplates, at least part of the second fixation surface including a stepped form.

According to a further feature of the present invention, the implant structure is a rigid spacer providing a second fixation surface for fixation to the other of the vertebral endplates, the second fixation surface being in fixed spatial relation to the first fixation surface.

According to a further feature of the present invention, the implant structure is a total disc replacement including at least two of the implant elements interconnected by a joint arrangement.

According to a further feature of the present invention, the joint arrangement includes a ball-and-socket joint.

According to a further feature of the present invention, the joint arrangement includes a flexible cushion.

According to a further feature of the present invention, the joint arrangement is configured to generate distraction of an intervertebral spacing between the superior and inferior vertebral bodies as a smooth function of angular displacement from a neutral position over at least part of a range of motion in each of at least two independent directions of angular displacement.

BRIEF DESCRIPTION OF THE DRAWINGS

The invention is herein described, by way of example only, with reference to the accompanying drawings, wherein.

DESCRIPTION OF THE PREFERRED EMBODIMENTS

The present invention is an intervertebral implant with stepped or tiered fixation surfaces to provide stable load support via cortical bone and endplate tissues combined with effective short-term and long-term locking against implant migration.

The principles and operation of intervertebral implants according to the present invention may be better understood with reference to the drawings and the accompanying description.

By way of introduction, the present invention provides various combinations of features for use in bone fixation surfaces for intervertebral implants. These features are applicable to all types of intervertebral implants, including articulated intervertebral disc replacements of all types and rigid intervertebral spacers of all types. In one particularly preferred set of non-limiting embodiments presented below with reference to FIGS. 1A-4A and 9A-9E, the invention is implemented with an intervertebral disc replacement according to the teachings of co-pending international patent application no. PCT/IL07/000239 which was unpublished prior to the date of filing of this application and does not constitute prior art to this application, and from which the present application claims priority. A number of additional non-limiting examples of implants including bone fixation surfaces according to the teachings of the present invention are illustrated in the remaining FIGS. 5A-8E and 10A-12E.

Figure 1A:
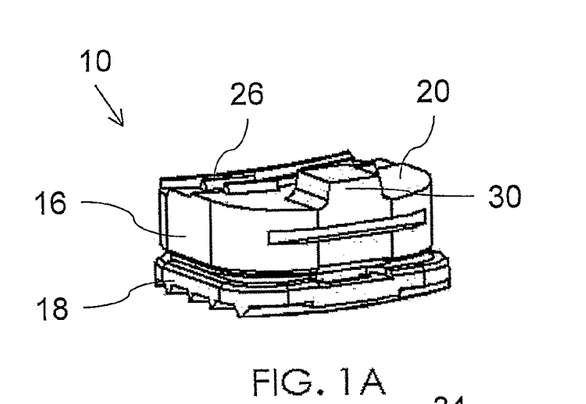
FIG. 1A is a ventral isometric view of an intervertebral implant, in this case a intervertebral disc replacement, constructed and operative according to the teachings of the present invention, showing a superior fixation surface.
Figure 1B:
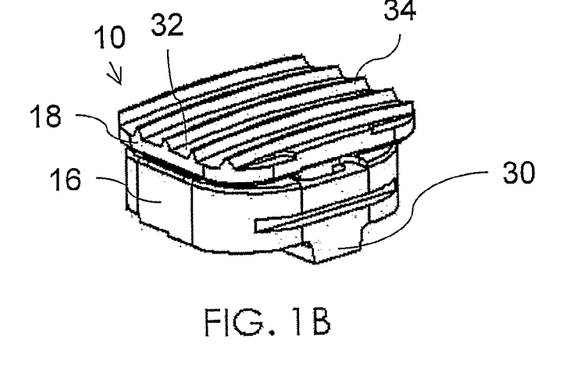
FIG. 1B is an inverted isometric view of the intervertebral implant of FIG. 1A showing an inferior fixation surface.
Figure 1C:
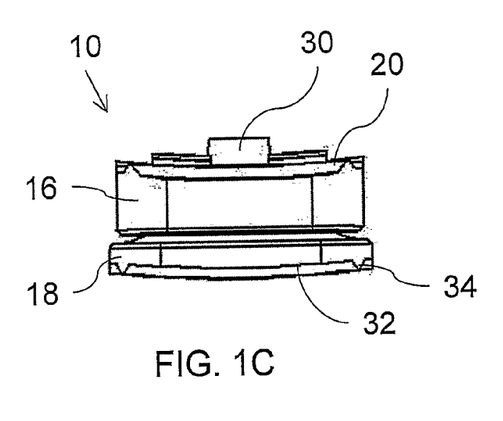
FIG. 1C is a dorsal view of the intervertebral implant of FIG. 1A.
Figure 1D:
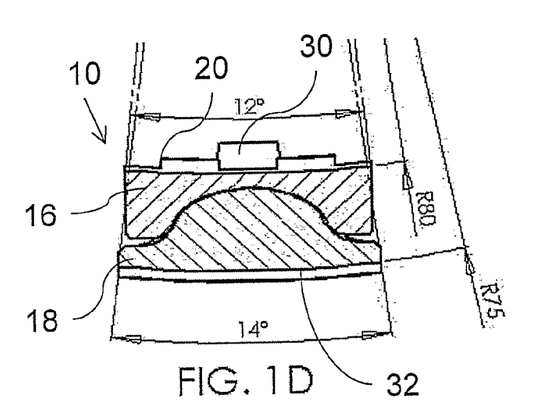
FIG. 1D is a coronal cross-section taken through the intervertebral implant of FIG. 1A.
Figure 2A:
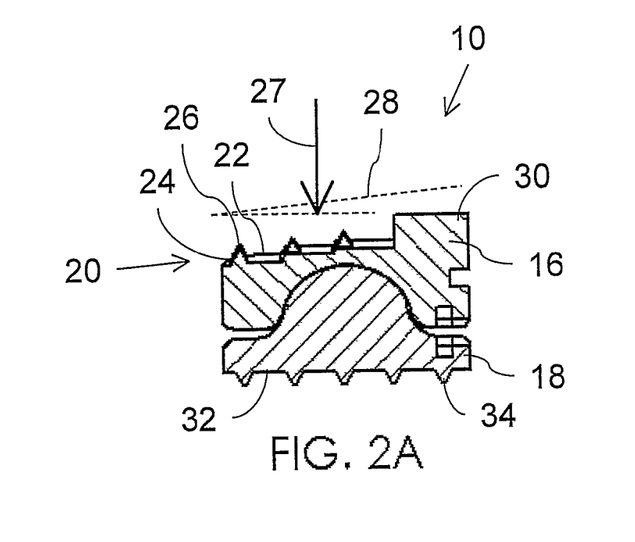
FIG. 2A is a sagittal cross-section taken through the intervertebral implant of FIG. 1A.
Figure 2B:
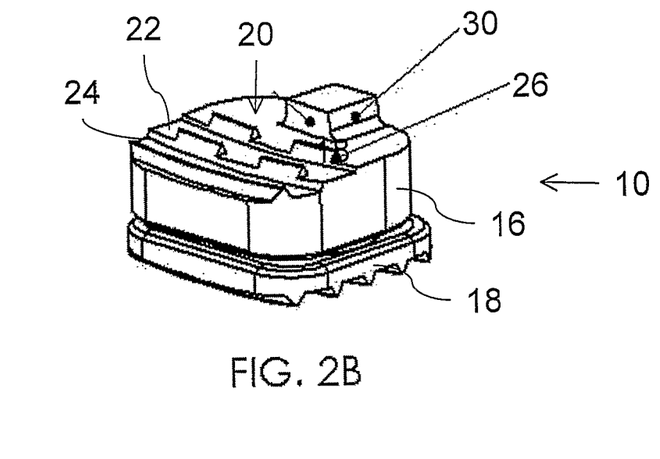
FIG. 2B is a dorsal isometric view of the intervertebral implant of FIG. 1A.
Figure 2C:
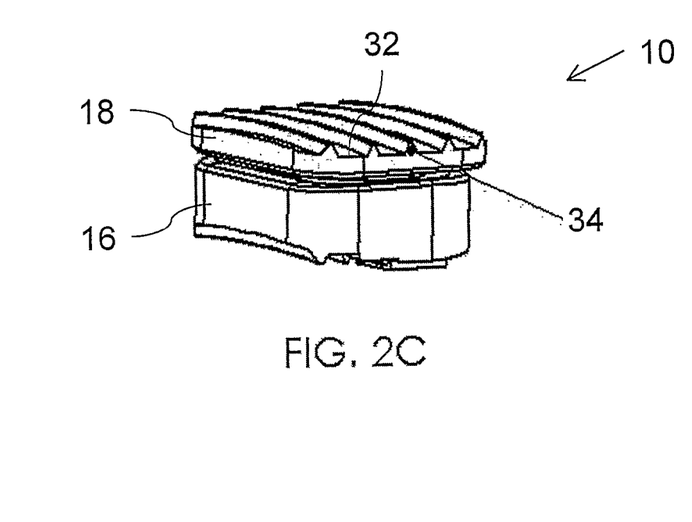
FIG. 2C is an inverted dorsal isometric view of the intervertebral implant of FIG. 1A.
Figure 3A:
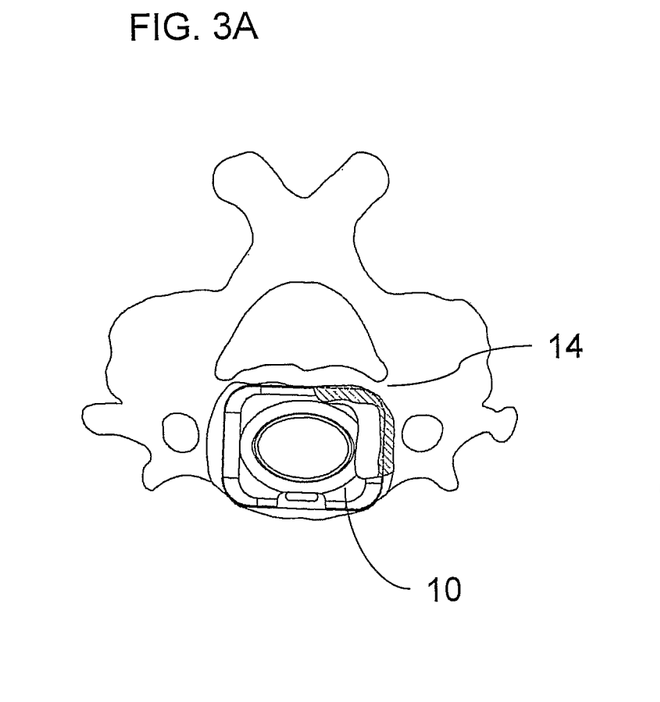
FIG. 3A is a plan view of a cervical vertebral body showing the positioning of the intervertebral implant of FIG. 1A.
Figure 3B:
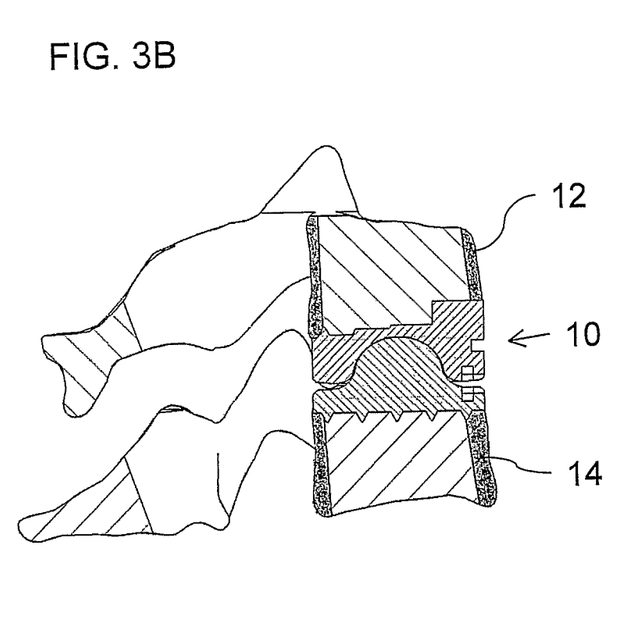
FIG. 3B is a sagittal cross-sectional view taken through two adjacent cervical vertebral bodies between which the intervertebral implant of FIG. 1A has been implanted.

Referring now to the drawings, FIGS. 1A-4A illustrate a first embodiment of an intervertebral implant 10, constructed and operative according to the teachings of the present invention, for deployment as shown in FIG. 3B between an inferior endplate of a superior vertebral body 12 and a superior endplate of an inferior vertebral body 14 of a spinal column. In this case, implant 10 corresponds to the first embodiment of an intervertebral disc replacement described in the aforementioned co-pending international patent application no. PCT/L07/000239, which is hereby incorporated in its entirety. The articulation surfaces of implant 10, which are not directly relevant to the invention as claimed herein, are described in detail in the above-referenced document, and for brevity will not be addressed extensively here.

Figure 4A:
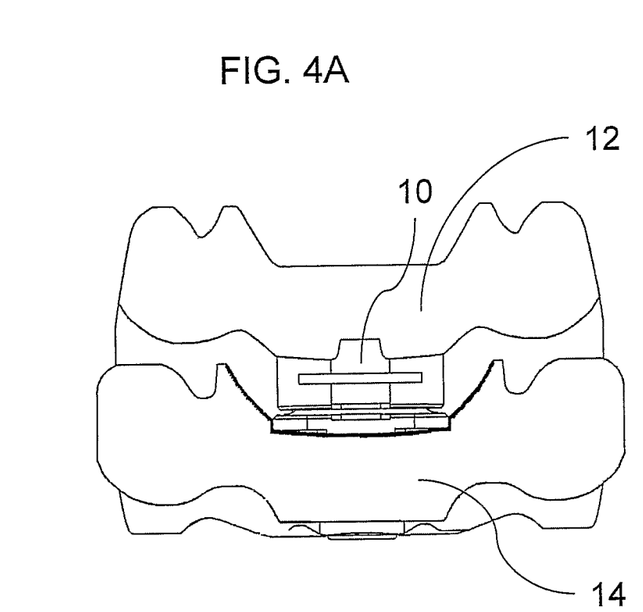
FIG. 4A is a ventral view of the vertebral segment of FIG. 3B showing the deployment of the intervertebral implant of FIG. 1A.

Generally speaking, implant 10 has a structure including at least one, and in this case two, implant elements: an upper element 16 and a lower element 18. Upper element 16 provides a first fixation surface 20 for fixation to the inferior endplate of the superior vertebral body. It is a particular feature of most preferred implementations of the present invention that fixation surface 20 includes a primary load-bearing region extending at least around a major part of a periphery of the first fixation surface, and in this case, over substantially the entirety of fixation surface 20. This primary load-bearing region exhibits a generally concave form in a lateral-lateral direction, as best seen in FIGS. 1C, 1D and 4A, and a generally stepped or tiered form in an anterior-posterior direction, as best seen in FIGS. 2A and 3B. More specifically, referring to FIG. 2A, the generally tiered form includes a plurality of load-bearing surfaces 22 separated by step surfaces 24, together forming a series of steps which provide a transition from a relatively higher anterior (or medial) region of the surface and a relatively lower posterior region.

At this stage, it will already be appreciated that the structure of fixation surface 20 provides a highly advantageous combination of features. Specifically, the use of steps to achieve variation in axial height of the bone contact surfaces in at least one direction rather than the more intuitive sloped surfaces provides immediate purchase of the non-sharp edges of the steps by press-fitting against the bone. As the surface becomes more settled into the bone under applied loading and osteo-integration occurs, the resulting stepped interlocking bone-implant interface provides highly effective resistance to linear and rotary migration of the implant. These and other advantages of the present invention will be better understood in view of the following detailed description.

Before referring to further details of preferred implementations of the present invention, it will be useful to define certain terminology as used herein in the description and claims. Firstly, the load-bearing region is referred to as "extending at least around a major part of a periphery of the first fixation surface." This language is used to define a minimum extent of the load-bearing region, namely, extending inwards from the outer periphery of the fixation surface around the majority, and typically substantially the entirety, of the periphery. The peripheral extent of the load-bearing region is preferably only interrupted by the presence of one or more anchoring projection, as will be described below. The inward extent of the load-bearing region is chosen to be sufficient to cooperate effectively with the cortical bone tissue so as to transfer most of the load via the structurally strong cortical bone, as illustrated in FIG. 3B, and is typically at least about 2 millimeters.

The phrases "stepped form" and "tiered form" are used herein interchangeably in the description and claims to refer to a form in which, when viewed in cross-section in at least one direction, horizontal surfaces, or shallowly inclined surfaces, located at different levels are connected by more steeply inclined or vertical surfaces. In preferred cases, the horizontal spacing between adjacent steps is greater than the height of the steps. Preferably, the shallowly inclined surfaces are inclined at no more than about 20 degrees to an axial plane, and more preferably no more than 10 degrees thereto. The more steeply inclined surfaces are preferably inclines at no less than 45 degrees, and more preferably, at least about 60 degrees, to an axial plane. An edge angle formed between the surfaces is preferably no less than 90 degrees.

Although the preferred embodiments illustrated herein provide a stepped form in the anterior-posterior direction, i.e., where the length of the steps extends laterally, the invention is not limited to such an example, and any direction, or a combination of different directions of the steps may be used. Furthermore, the steps need not be straight. It should be noted that the stepped form may be in a region which has a gradient or otherwise complex form in the direction parallel to the steps. Any reference to the steps being "parallel", or a spacing between the steps, refers to the geometry as viewed in plan (axial) view. Similarly, the steps may be curved as viewed in plan view.

The load-bearing surfaces 22 are described herein as arranged to provide non-migratory support. The phrase "non-migratory support" is used herein in the description and claims to refer to surfaces deployed so as to oppose axial loading without generating a significant shear effect which would tend to generate migration of the intervertebral insert in an axial plane. More specifically, the load-bearing surfaces 22 are preferably deployed without significant inclination in an anterior-posterior direction. In the lateral-lateral direction, the support surfaces are preferably formed with symmetrical inclination (which may vary along their length) so as to provide centering of the vertebral body endplate while still avoiding generating migratory forces. The details of various exemplary embodiments will be described more fully below.

Reference is also made to an "effective lordosis plane" which corresponds to the overall orientation imparted to the vertebral body endplate against which fixation surface 20 is engaged. Geometrically, the effective lordosis plane may be regarded as the "best-fit plane" approximating to the anterior-posterior profile of the fixation surface, and neglecting any localized anchoring projections or other features for which counter-sunk recesses are to be cut. The "best-fit" may be defined according to any suitable best-fit criteria including, but not limited to, a "least squares" approximation, as is well known in the art.

The effective lordosis plane is referred to as "inclined" relative to the primary load-bearing direction. The term "inclined" is used to refer to two lines, a line and a plane, or two planes which are non-parallel and non-perpendicular.

Various projecting features of the fixation surfaces of the present invention are referred to as "non-sharp." The phrase "non-sharp" is used herein in the description and claims to refer to features which do not exhibit points or edges presenting angles less than 30 degrees, and preferably for which all edges present angles of at least 45 degrees. Such non-sharp projections are believed to offer more stable long-term osteo-integration than is achieved by sharp projections.

Where reference is made to the relative orientation of features or surfaces on the upper and lower fixation surfaces, these are clearly well defined in the case of a spacer (i.e., with fixed geometrical relation between the upper and lower fixation surfaces), but must be carefully defined for intervertebral disc replacements, which allow relative motion of the upper and lower fixation surfaces. In such cases, the relative orientations should be understood to refer to a "neutral position" of the intervertebral disc replacement. This neutral a position is taken to be the normal un-flexed state of the apparatus when implanted within a spinal column. In cases in which the inward-facing articulation surfaces of the upper and lower members include substantially flat peripheral regions, the neutral position preferably corresponds to a substantially parallel state of the flat regions. In certain particularly preferred embodiments, the apparatus is self-biasing under axial loading so as to return towards the neutral position.

Various features will be referred to herein as "recesses" or "projections". It should be noted that the terms "recess" and "concave" are used herein to refer to a surface which can be sealed by addition of a single plane to enclose a volume. A recess thus defined includes recesses which may have local projecting or convexly curved features within them. Conversely, a "projection" or "protuberance" from a surface, or a convex surface, is defined as a part of a body which could be severed from the underlying surface by cutting along a single plane, independent of whether the surface of the projection or protuberance includes localized recesses or concavely curved features. Where a surface is referred to as concavely curved or convexly curved "in a given direction", the intention is that a cross-section taken in through the surface parallel to the given direction exhibits the described curvature.

For the most part, the terminology used when describing the geometry of the apparatus of the present invention is the medical terminology, although this terminology may be used interchangeably with alternative mechanical terminology at times. The medical terminology is to be interpreted according to the context of the intended location and orientation in which the device is to be deployed in the body, although the terminology is used to refer to the device when standing alone. Thus, a central vertical plane passing front-to-back through the device is termed "sagittal" while a cross-ways vertical plane passing side-to-side is termed "coronal" and a horizontal plane is termed "axial". Similarly, a front view is termed "ventral", a rear view "dorsal", a side view "lateral" and a top view "axial".

Regarding types of motion, here too preference is given to the normal medical terminology for the corresponding body movements. Thus, bending forward is "(anterior) flexion", bending backwards is "(posterior) extension", bending sideways is "lateral bending", and twisting to the sides is "axial rotation". For convenience, reference may be made to "axes" of deflection or rotation, which are side-to-side for flexion and extension, front-to-back for lateral bending and vertical for axial rotation. It should be noted however that, depending upon the type of disc replacement used, these motions may not be pure rotations about a fixed axis, but rather more complex motions in which the effective center of rotation shifts during the course of the motion. A linear directions front-to-back is referred to as "anterior-posterior", and side-to-side is "lateral-lateral."

It will also be noted that wherever reference is made to motion of a disc replacement, this is relative motion between the first and second members of the apparatus, corresponding to the motion superior and inferior vertebrae to which the respective members are fixed. For convenience, the motion may be referred to herein as if the lower member is fixed in a horizontal plane and the upper member moves. Clearly, when the apparatus is implanted in the body, the actual orientation of the members will be the local orientation of the relevant vertebral segment, with the apparatus working in cooperation with other vertebral segments (with either natural discs or additional apparatuses according to the present invention) to provide the overall total motion properties required of the spinal column.

When reference is made to "first" and "second" members, unless otherwise stated, it should be assumed that the features described may be applied interchangeably to the superior (upper) and inferior (lower) members.

Used in the context of vertebral bodies, the terms "first" and "second" are used herein in the description and claims as non-specific labels to refer to any pair of adjacent vertebral bodies between which the apparatus of the present invention is to be inserted. In fact, with suitable choice of dimensions and geometry, the present invention may be employed to advantage at one location or multiple locations throughout the cervical, thoracic and lumbar regions of the spinal column, from the joint of cervical vertebrae C2/C3 through to the bottom lumbar joint of L5/S1.

Finally with respect to definitions, in the context of particularly preferred implementations employing an intervertebral disc replacement according to the teachings of co-pending international patent application no. PCT/IL07/000239, reference is made to an intervertebral spacing varying as a "smooth function" of angular displacement from the neutral position. The term "smooth function" is used herein to refer to any function which can be differentiated at all points within the relevant range. In other words, the variation of intervertebral spacing with angular displacement is "smooth" in that it does not have any abrupt changes in gradient. As a result, the restoring moment acting as a result of axial loading, corresponding to the derivative of the intervertebral spacing with respect to angle, does not have any sudden steps, and the motion attenuation is therefore non-impact attenuation.

Turning now to the features of the present invention in more detail, the anterior-posterior profile of fixation surface 20 are best seen in FIGS. 2A and 2B. Load-bearing surfaces 22 are preferably arranged to provide non-migratory support against loading in a primary load-bearing direction (arrow 27), while the generally tiered form preferably defines an effective lordosis plane 28 inclined relative to the primary load-bearing direction 27. Thus, the tiered structure provides a correctly oriented effective lordosis plane 28 while at the same time ensuring that load-bearing surfaces 22 are correctly oriented to provide support against applied axial loads without generating secondary lateral forces.

As described above, in addition to addressing the angular offset between the primary loading direction and the angle of effective lordosis, the combination of load-bearing surfaces 22 and step surfaces 24 provides an anti-migration bone engaging configuration which is believed to be highly advantageous, even if used at different angles. Specifically, surfaces 22 and 24 serve as pairs of elongated surfaces converging to a crest. Unlike conventional keels or sharp ridges which are either countersunk or cut into the bone surface, these angular crests lodge against the surface of the bone and become press-fit against the bone under subsequent loading. The result is a bone-implant interface which takes on an intimately inter-engaged pattern of crests and troughs, thereby providing highly effective anchoring against migration. To provide this anchoring, the width dimensions of the pairs of surfaces measured perpendicular to the length of the crest, corresponding to the distance between the steps, is preferably at least about 5 percent, and more preferably at least about 7 percent, of a posterior-anterior dimension of the first fixation surface.

At the same time, the width dimensions of the pairs of surfaces measured perpendicular to the length of the crest, corresponding to the distance between the steps, is preferably no more than 40 percent, and more preferably no more than about 15 percent, of a posterior-anterior dimension of the first fixation surface. Thus, the interface geometry preserves an overall profile matched to the natural bone surface form and does not typically require significant preparation or reshaping of the bone surface (except for minor press-fit anchoring projections where present, such as will be described below).

In actual dimensions, a preferred width of the pairs of elongated surfaces is typically in the range from about 2 to about 4 millimeters, and a maximum depth of the troughs between crests is preferably between about 0.5 and about 2 millimeters. The crests are preferably non-sharp crests, and are preferably modified by the presence of ridges, as will be described below.

In the preferred case shown here, the crests are substantially parallel so as to form the generally stepped or tiered form described above. However, it should be noted that other forms of deployment of the surfaces, and the resulting crests, are also possible. Examples include, but are not limited to, crests extending radially outwards from a central region, patterns with various directions of crests such as in concentric polygons, and various curved patterns of crests.

As mentioned before, in the particularly preferred case of parallel crests, surfaces 22 are preferably arranged to provide non-migratory support against loading in a primary load-bearing direction, while the generally tiered form defines an effective lordosis plane inclined relative to the primary load-bearing direction. In this case, surfaces 22 and 24 define what is referred to here as a tiered or stepped form.

In addition to the tiered overall profile defined by load-bearing surfaces 22 and step surfaces 24, the primary load-bearing region preferably further includes a plurality of non-sharp projecting ridges 26 extending substantially parallel, and adjacent, to the steps or crests formed between surfaces 22 and 24. In a particularly preferred implementation as shown here, each projecting ridge 26 has a flank surface which runs into one of step surfaces 24. In other words, one flank of the ridge is either coplanar with step surface 24, or intersects therewith at a change of gradient. In the preferred case shown here, ridges 26 are formed with an upper edge angle of about 60 degrees, and each step surface 24 is angled at about 60 degrees to the load-bearing surfaces 22, with step surface 24 and one face of ridges 26 forming a continuous planar surface.

Projecting ridges 26 preferably do not all extend across the entirety of the implant, but rather terminate at end surfaces 28 (see FIG. 2B) deployed to inhibit lateral migration of the implant. Thus, in the preferred example shown, two projecting ridges 26 are provided along the edge of each step, each providing two opposite-facing end surfaces 28. While the ridge nearest the posterior extreme of fixation surface 20 may also have interruptions to form end surfaces, in the particularly preferred case illustrated here, the posterior ridge is continuous across the width of fixation surface 20 in order to maximize the surface for osteointegration with the hard cortical bone of the vertebral body.

Additional fixation against linear and rotational migration is preferably formed by providing fixation surface 20 with at least one press-fit anchoring projection 30. Press-fit anchoring projection 30 has an axial (height) dimension smaller than both its anterior-posterior and its lateral-lateral dimensions, and is preferably formed with at least two opposing faces inclined to provide a wedge angle of between 1 degree and 30 degrees, and typically between about 5 and 15 degrees. Most preferably, anchoring projection 30 is formed with corner regions deployed to provide anchoring against axial rotational migration of the intervertebral implant. A rectangular shape in axial view is typically preferred. A complementary recess in the vertebral body is typically formed by use of standard tools, such as a Kerrison punch.

Since the normal surgical approach for implantations of the devices of the present invention is a ventral approach, anchoring projection 30 is preferably located on the anterior periphery of the device, either in the form of a single projection as shown, or a pair of spaced apart projections (see FIGS. 8A-8E, below).

Referring now particularly to FIGS. 1C, 1D and 4A, these illustrate clearly the preferred form of fixation surface 20 in a lateral-lateral direction for supporting a cervical vertebral body. In all embodiments of the present invention, the primary load-bearing region preferably exhibits upward-turned edges towards the lateral periphery of the fixation surface, which give a generally concave outer profile as seen in dorsal view. This concave outer profile has a centering effect on the superior vertebral body and helps to provide for stable and effective transfer of loading between the implant and the cortical bone of the superior vertebral body. The central part of the fixation surface is formed to play only a minor or even negligible part in the transfer of loading, and yet to follow closely the shape of the adjacent vertebral body endplate in order to accelerate osteo-integration over a large surface and to provide better fixation and anti-migration qualities for the entire device. In the case of a cervical implant, a continuous roughly arcuate concave form in the lateral-lateral direction is believed to provide both the peripheral support and the central proximity to the vertebral endplate. Thus, the fixation surface 20 may here be considered to be a single continuous surface in which the structural features of the primary load-bearing region extend over substantially the entirety of the fixation surface. The concave shape in the lateral-lateral direction helps to provide migration resistance to the device in the lateral direction. Once the device is fixed within the intervertebral space, the generally concave geometry of the upper fixation surface 20 enhances its fixation and reduces the chance of lateral slippage. The arcuate shape provides a niche in which the entire vertebral endplate is received, and encourages attachment in a balanced self-centering manner under the influence of the natural spinal column alignment and predominantly axial natural loading force applied on the spinal column. A radius of curvature of between about 6 and about 10 centimeters, and most preferably about 8 centimeters is typically suitable, and an angular deflection of between about 10 degrees and about 15 degrees, and most preferably about 12 degrees, from side to side.

Figure 4B:
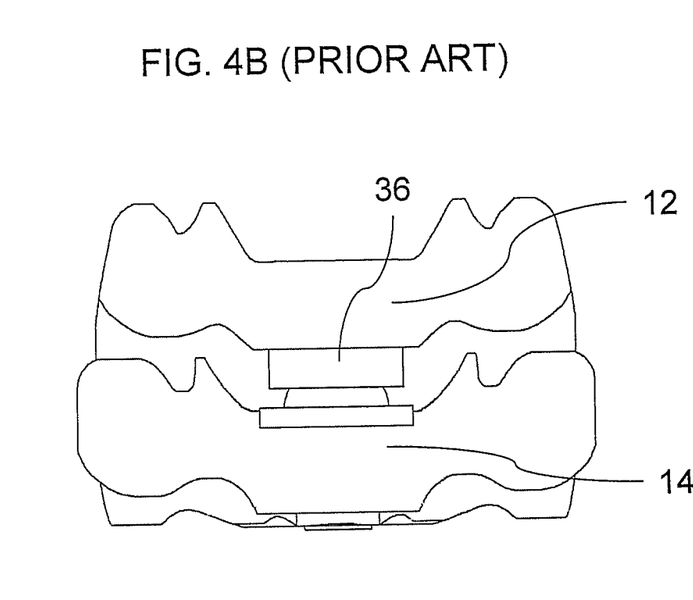
FIG. 4B is a ventral view similar to FIG. 4A showing for comparison the deployment of a commercially available ball-and-socket type intervertebral disc replacement.
Figure 5A:
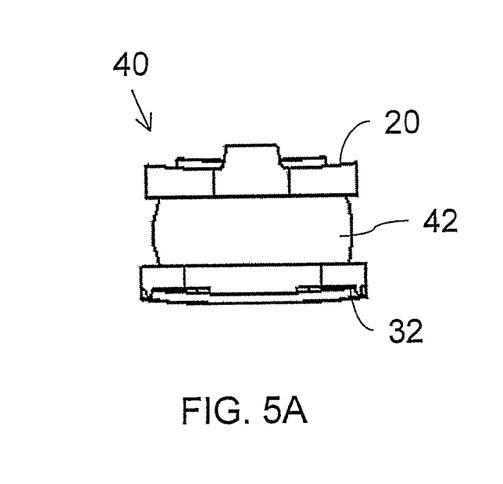
FIGS. 5A-5E are ventral, lateral, dorsal, isometric and inverted isometric views, respectively, of an alternative embodiment of an intervertebral implant, in this case an intervertebral disc replacement including a flexible cushion, constructed and operative according to the teachings of the present invention.
Figure 5B:
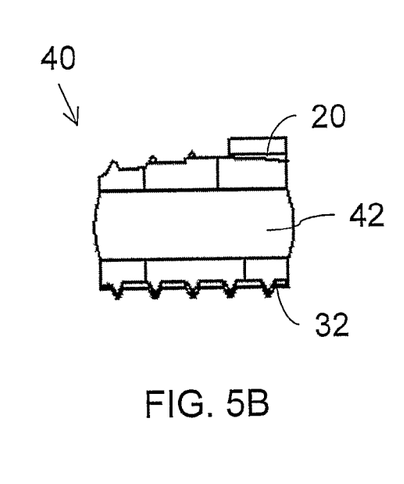
Figure 5C:
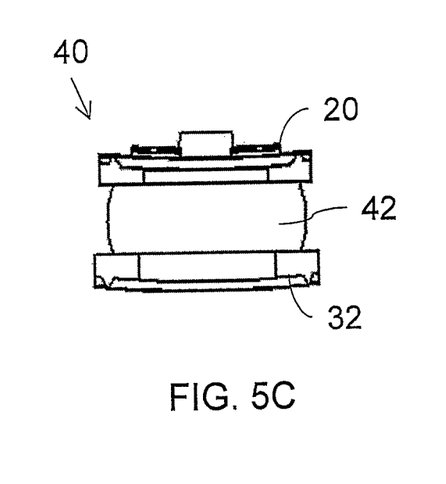
Figure 5D:
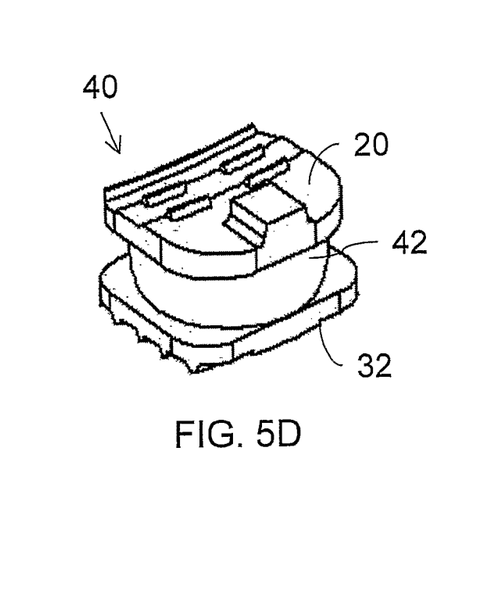
Figure 5E:
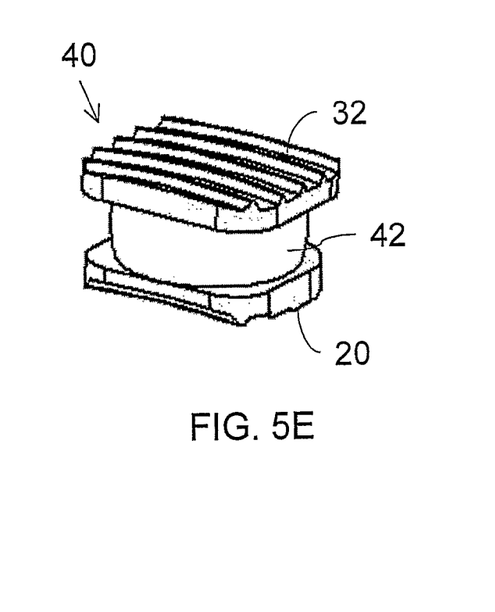
Figure 6A:
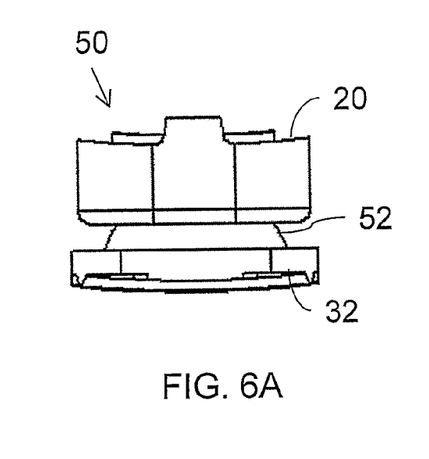
FIGS. 6A-6E are ventral, lateral, dorsal, isometric and inverted isometric views, respectively, of a further alternative embodiment of an intervertebral implant, in this case an intervertebral disc replacement including a ball-and-socket joint, constructed and operative according to the teachings of the present invention.
Figure 6B:
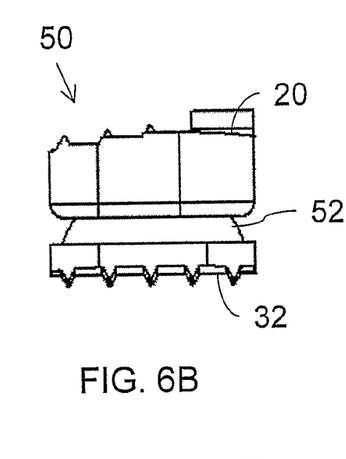
Figure 6C:
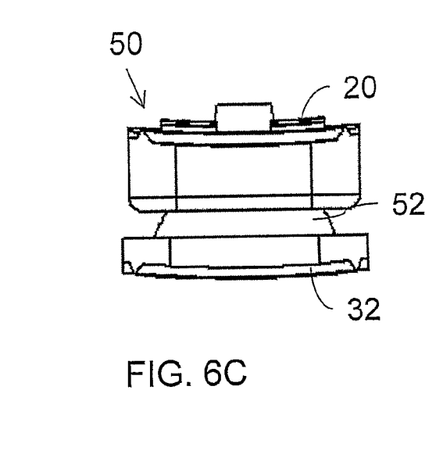
Figure 6D:
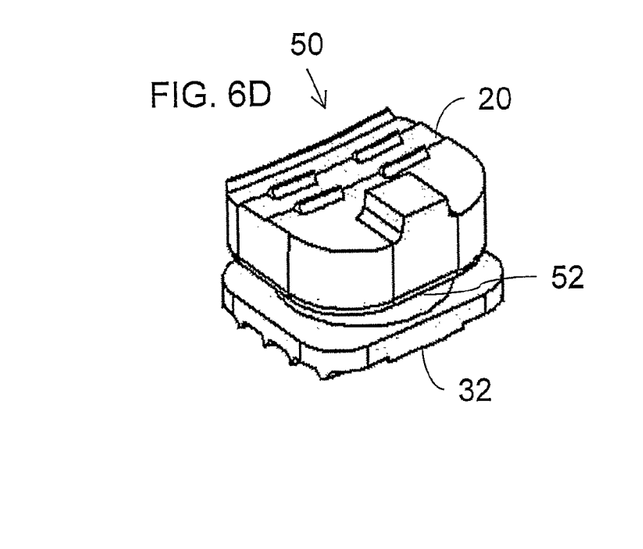
Figure 6E:
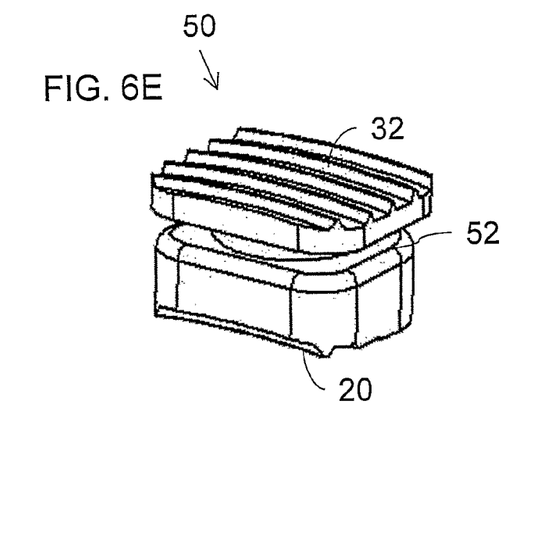
Figure 7A:
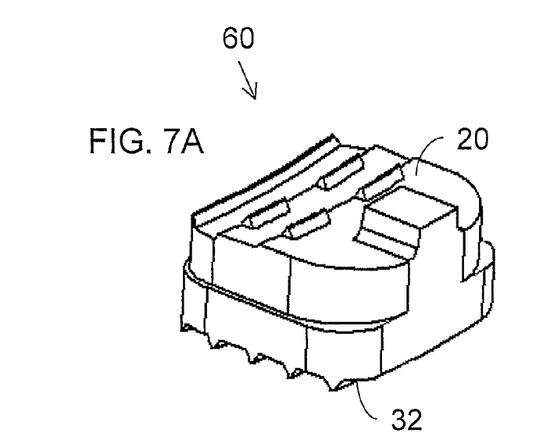
FIGS. 7A-7E are isometric, inverted isometric, ventral, lateral and dorsal views, respectively, of an alternative embodiment of an intervertebral implant, in this case an intervertebral spacer, constructed and operative according to the teachings of the present invention.
Figure 7B:
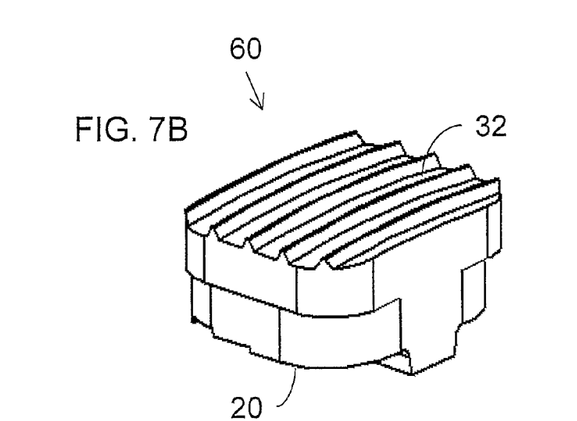
Figure 7C:
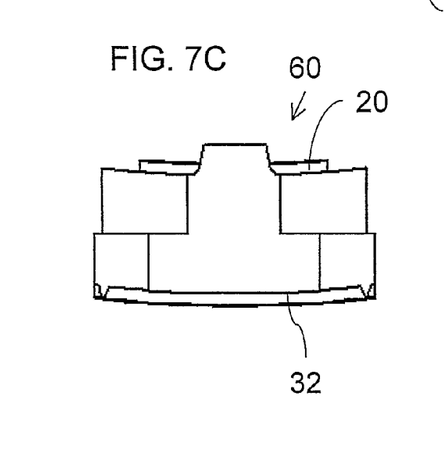
Figure 7D:
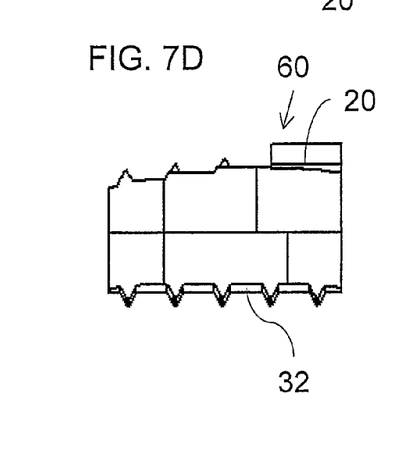
Figure 7E:
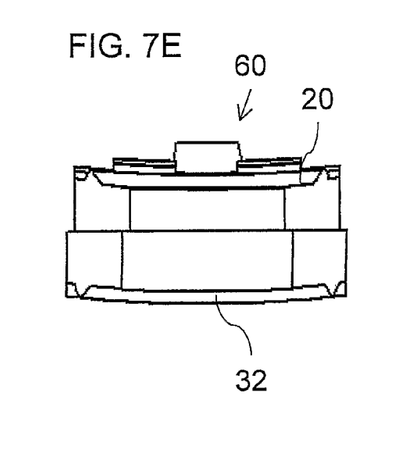
Figure 8A:
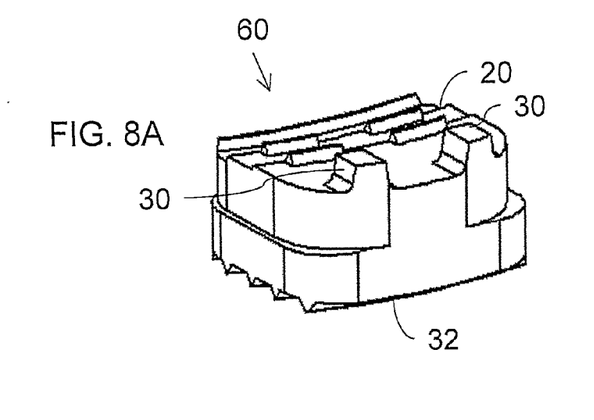
FIGS. 8A-8E are isometric, inverted isometric, ventral, lateral and dorsal views, respectively, of an intervertebral spacer similar to that of FIGS. 7A-7E, illustrating an alternative configuration of press-fit anchoring projections.
Figure 8B:
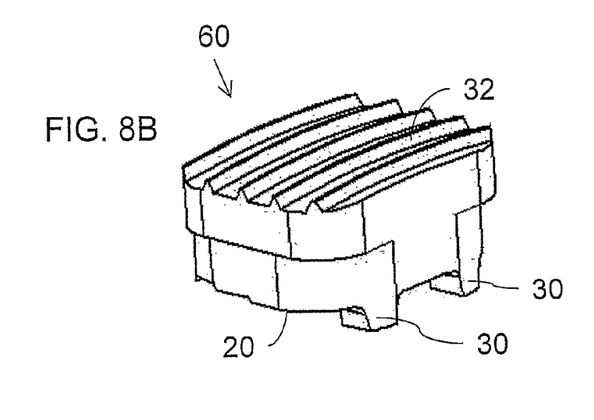
Figure 8C:
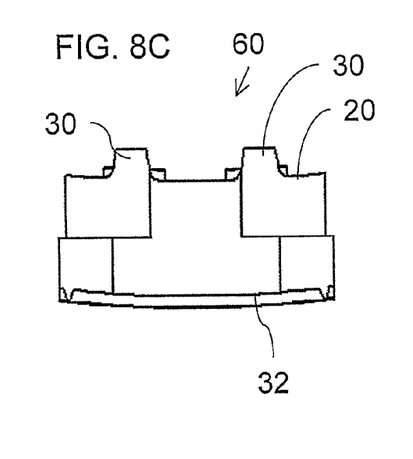
Figure 8D:
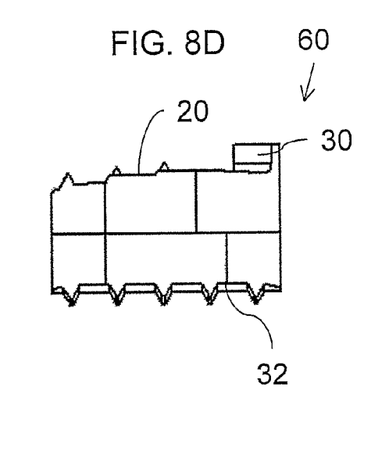
Figure 8E:
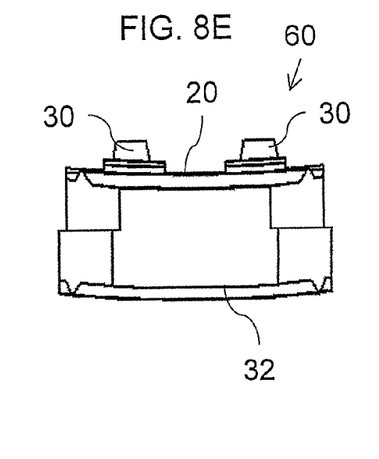
Figure 9A:
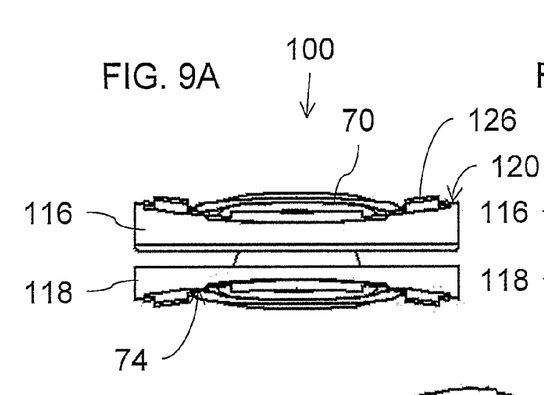
FIGS. 9A-9E are dorsal, lateral, ventral, ventral isometric and dorsal isometric views, respectively, of an alternative embodiment of an intervertebral implant, in this case an intervertebral lumbar disc replacement conceptually similar to that of FIGS. 1A-4A, constructed and operative according to the teachings of the present invention.
Figures 9B, 9C:
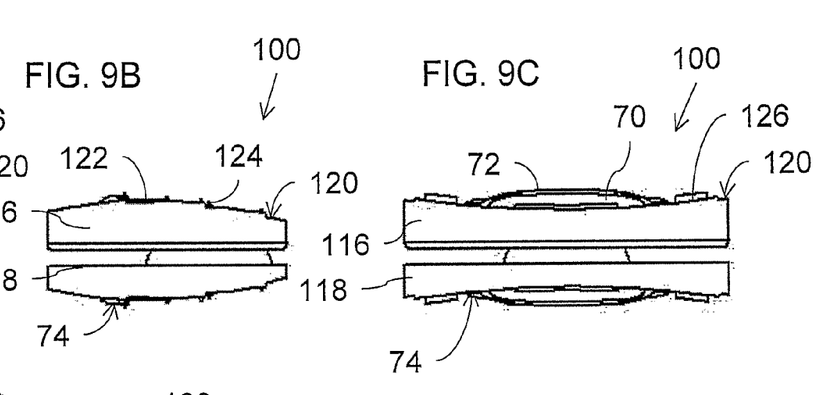
Figure 9D:
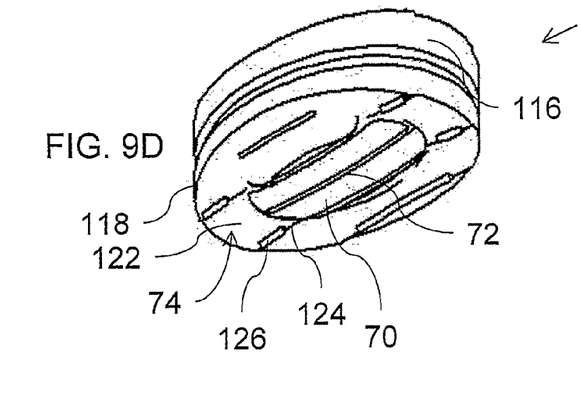
Figure 9E:
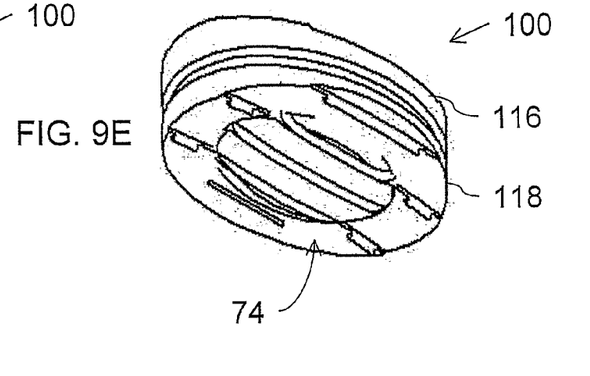
Figure 10A:
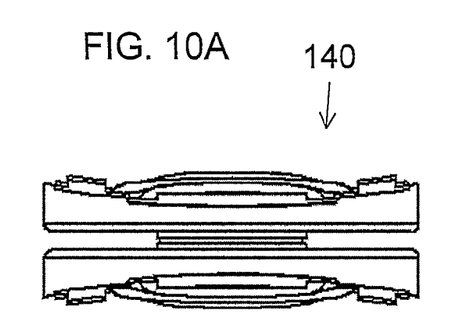
FIGS. 10A-10E are dorsal, lateral, ventral, ventral isometric and dorsal isometric views, respectively, of a further alternative embodiment of an intervertebral implant, in this case an intervertebral lumbar disc replacement including a flexible cushion, constructed and operative according to the teachings of the present invention.
Figure 10B:
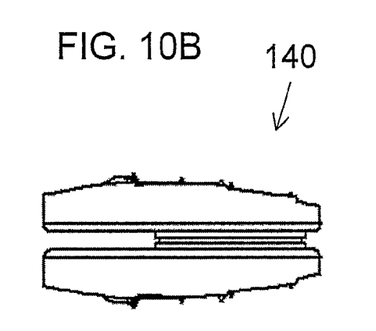
Figure 10C:
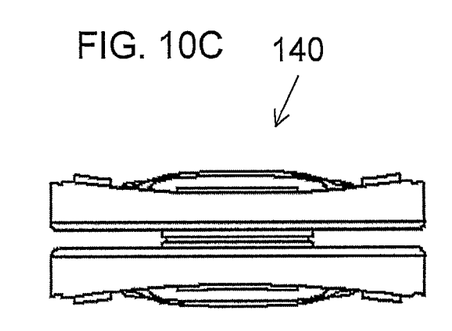
Figure 10D:
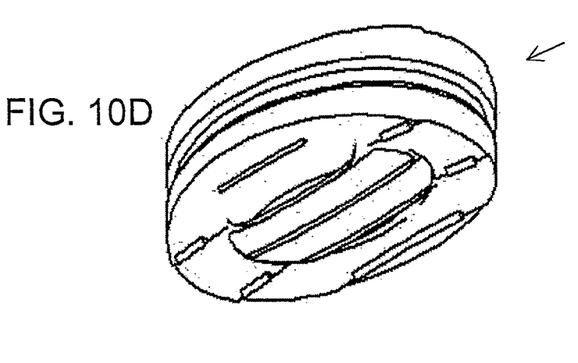
Figure 10E:
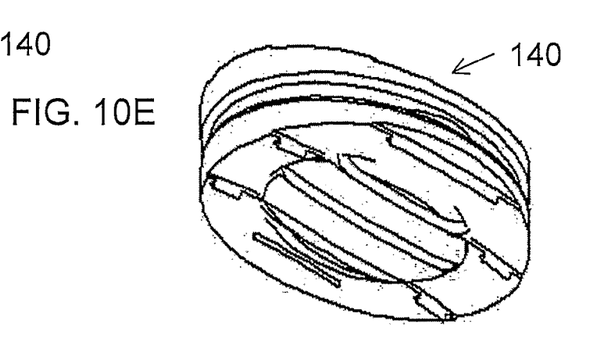
Figure 11A:
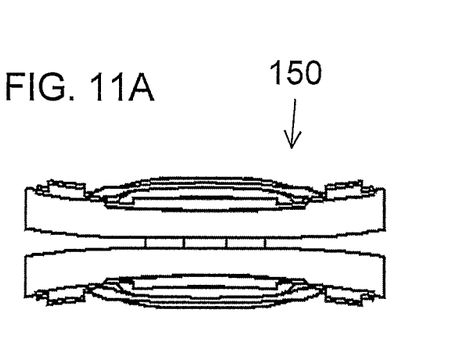
FIGS. 11A-11E are dorsal, lateral, ventral, ventral isometric and dorsal isometric views, respectively, of a still further alternative embodiment of an intervertebral implant, in this case an intervertebral lumbar disc replacement including a ball-and-socket joint, constructed and operative according to the teachings of the present invention.
Figure 11B:
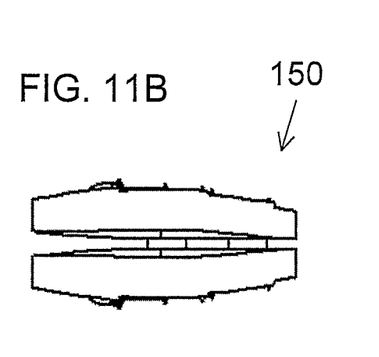
Figure 11C:
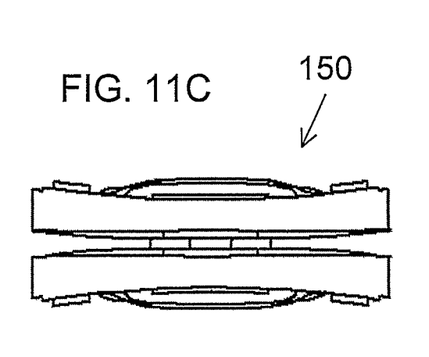
Figures 11D, 11E:
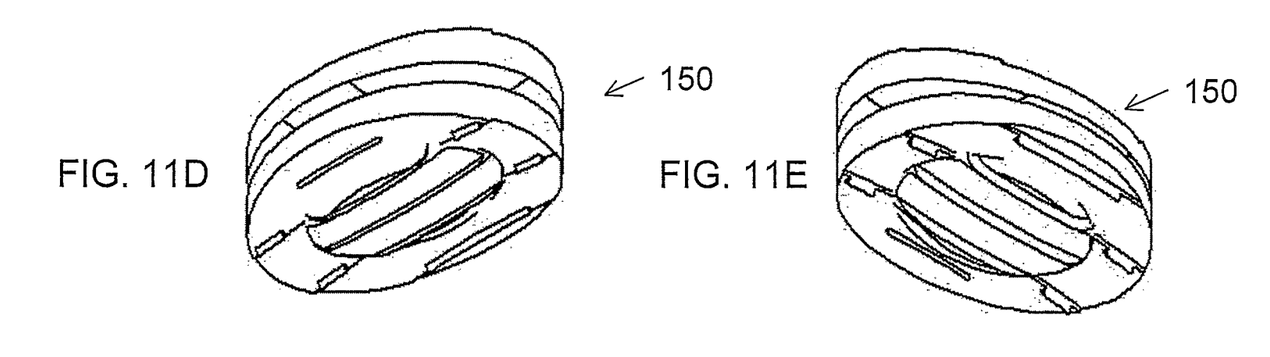
Figure 12A:
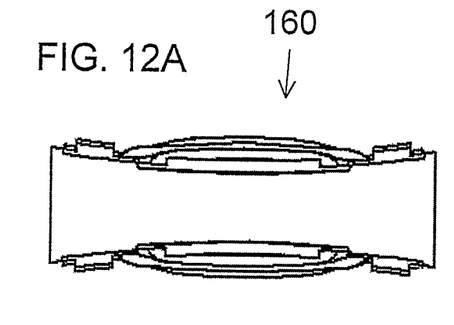
FIGS. 12A-12E are dorsal, lateral, ventral, lateral isometric and dorsal isometric views, respectively, of a further alternative embodiment of an intervertebral implant, in this case a lumbar intervertebral spacer, constructed and operative according to the teachings of the present invention.
Figure 12B:
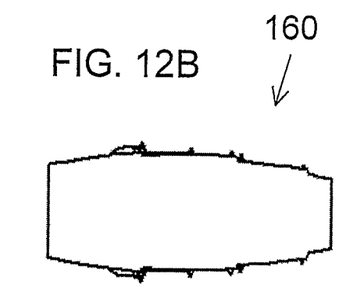
Figure 12C:
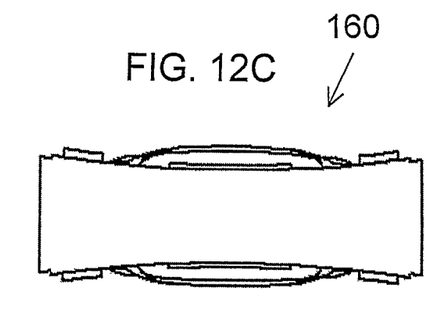
Figure 12D:
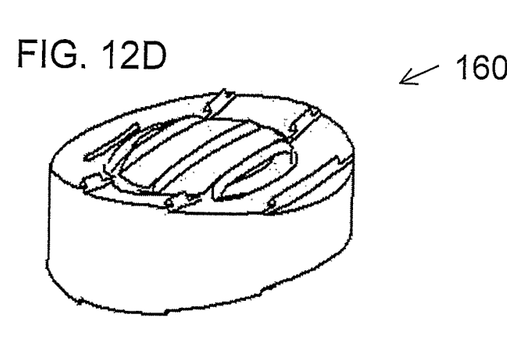
Figure 12E:
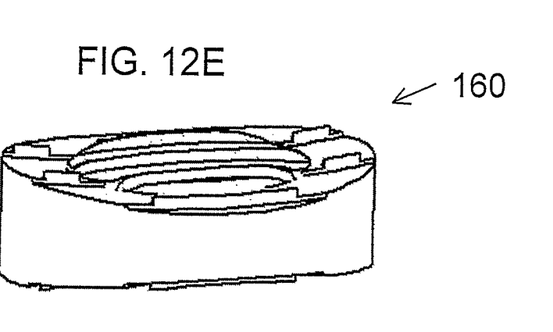

Referring parenthetically to FIG. 4B, this shows for comparison the geometry of the bone contact surfaces for an exemplary commercially available ball-and-socket intervertebral disc replacement 36. Comparing this drawing with FIG. 4A, it is apparent that the relatively smaller and flat bone contact surface of the prior device lacks the self-centering properties of the peripherally concave profile of fixation surface 20, and fails to concentrate the load on the cortical bone tissue.

Turning now to the lower side of intervertebral implant 10, second member 18 provides a second fixation surface 32 for fixation to the superior endplate of the inferior vertebral body 14. A preferred form for second fixation surface 32 in the case of a cervical intervertebral implant is illustrated in FIGS. 1B, 2A, 2C, 3B and 4A. Here too, second fixation surface 32 preferably includes a plurality of non-sharp ridges 34 extending in a lateral-lateral direction to oppose anterior or posterior migration. A generally convexly curved form in a lateral-lateral direction is preferably used, and at least the anterior part of the device is seated between the uncinate processes, as is known in the art, thereby anchoring the implant against lateral migration.

As mentioned earlier, the fixation features of the present invention are applicable to a wide range of intervertebral implants. By way of a first particularly preferred but non-limiting example, the invention has been illustrated thus far with reference to FIGS. 1A-4A in the context of an intervertebral disc replacement with a joint arrangement configured to generate distraction of an intervertebral spacing between the superior and inferior vertebral bodies as a smooth function of angular displacement from a neutral position over at least part of a range of motion in each of at least two and preferably three independent directions of angular displacement. Details of various examples of joint arrangements which provide this functionality are not per se part of the present invention, and may be found in the aforementioned co-pending international patent application no. PCT/IL07/000239. For conciseness, they will not be reproduced here.

By way of a first additional example, FIGS. 5A-5E show an embodiment of an intervertebral implant 40, constructed and operative according to the teachings of the present invention, which employs first and second fixation surfaces 20 and 32 as described above in the context of implant 10. In this case, implant 40 is an intervertebral disc replacement with a joint arrangement implemented as a flexible cushion 42. The flexible cushion referred to here may be any conventional cushion-type replacement disc joint arrangement, typically employing a solid, filled or hollow polymeric structure which may have an accordion-type structure or any other structure known for this purpose.

By way of a further additional example, FIGS. 6A-6E show an embodiment of an intervertebral implant 50, constructed and operative according to the teachings of the present invention, which employs first and second fixation surfaces 20 and 32 as described above in the context of implant 10. In this case, implant 50 is an intervertebral disc replacement with a joint arrangement implemented as a ball-and-socket joint 52. The ball-and-socket joint may be any type of commercially available ball-and-socket joint, with or without an additional polymeric envelope.

By way of a still further example, FIGS. 7A-7E show an embodiment of an intervertebral implant 60, constructed and operative according to the teachings of the present invention, which employs first and second fixation surfaces 20 and 32 as described above in the context of implant 10. In this case, implant 60 is a rigid intervertebral spacer in which second fixation surface 32 is in fixed spatial relation to first fixation surface 20. The intervertebral spacer may be a solid structure as shown, or may be formed as a partially or fully hollow "cage."

Referring briefly to FIGS. 8A-8E, this shows a variant of intervertebral spacer 60, equally applicable to other embodiments, in which first fixation surface 20 is formed with two anchoring projections 30. In other respects, this implementation is fully analogous to that of FIGS. 7A-7E.

Turning now to FIGS. 9A-12E, as mentioned earlier, the principles of the present invention are equally applicable to intervertebral implants for use throughout the spinal column. While the general principles of the invention indeed remain the same, the specific forms of the implants vary considerably according to the anatomical and mechanical needs of the different regions. The invention will now be illustrated with reference to a number of embodiments of lumber intervertebral implants. A first of these implants, an intervertebral disc replacement generally designated 100, constructed and operative according to the teachings of the present invention, is illustrated in FIGS. 9A-9E.

In many respects, intervertebral implant 100 is similar to intervertebral implant 10 described above. For conciseness of description, analogous features are labeled here with the corresponding reference numerals incremented by 100, and will not be described again in detail. Thus, intervertebral implant 100 features upper and lower members 116 and 118, and an upper fixation surface 120 with a tiered peripheral primary load-bearing region formed with load-bearing surfaces 122, steps 124 and ridges 126. As in the previous examples, the tiered profile provides effective short and long term fixation against migration, and a generally concave lateral-lateral profile provides centering and support for the adjacent cortical tissue of the vertebral body endplate. The tiered profile also preferably provides non-migratory support for axial loading combined with a required degree of lordosis.

The most striking distinctive features of the required geometry of a lumbar intervertebral implant compared to a cervical implant are that both the upper and the lower vertebral bodies in the lumbar region present endplates with significant concavities, and that these concavities are roughly symmetrical. Accordingly, the upper and lower fixation surfaces of implant 100 are formed with convex central regions 70 in order to maintain the desired proximity between the fixation surface and the vertebral body endplate. Preferably, the convex central region also features a tiered form in an anterior-posterior direction, i.e., with surfaces for opposing axial loading and steps reducing the thickness of the central region towards the posterior side to contribute to the effective lordosis angle of the implant. A plurality of non-sharp ridges 72 preferably extend along edges of steps of the tiered form. These structural features are believed to provide sufficient anchoring against linear and rotational migration of the implant such that additional anchoring projections such as projections 30 described above are not required.

Although shown here as a roughly spherical modified by the tiered structure, convex central region 70 may have any form suited to achieve the desired proximity and osteo-integration geometry desired for a given vertebral body endplate shape. Thus, for example, the projection may be warped to an asymmetrical shape, with the highest point significantly off center, or the form may include two or more superimposed roughly spherical portions of different radii of curvature.

As mentioned above, the lumbar vertebrae also present a recessed endplate structure at the superior endplate of the inferior vertebral body. Preferred implementations of the present invention therefore provide a second fixation surface 74, for fixation to the superior endplate of the inferior vertebral body, which is similar or even identical to the surface 120. The lordosis correction may be achieved exclusively through the geometry of either one of the upper and lower members, or may be divided between the two members. In other respects, the structure of second fixation surface 74 may be fully understood by reference to the description of surface 120 and its analogous predecessor 20 described above.

Turning now briefly to the remaining drawings, FIGS. 10A-10E illustrate an alternative embodiment of an intervertebral implant, in this case an intervertebral lumbar disc replacement, designated 140, constructed and operative according to the teachings of the present invention. Implant 140 includes a flexible cushion.

FIGS. 11A-11E illustrate a still further alternative embodiment of an intervertebral implant, in this case an intervertebral lumbar disc replacement, designated 150, constructed and operative according to the teachings of the present invention. Implant 150 includes a ball-and-socket joint.

Finally, FIGS. 12A-12E illustrate a further alternative embodiment of an intervertebral implant, in this case a lumbar intervertebral spacer, designated 160, constructed and operative according to the teachings of the present invention.

It will be appreciated that the above descriptions are intended only to serve as examples, and that many other embodiments are possible within the scope of the present invention as defined in the appended claims.

What is claimed is:

1. An intervertebral implant for deployment between an inferior endplate of a superior vertebral body and a superior endplate of an inferior vertebral body of a spinal column, the implant comprising an implant structure including at least one implant element, said implant structure providing an upper fixation surface for fixation to the inferior endplate of the superior vertebral body, said upper fixation surface being a closed surface including a first posterior bone contact region and a second anterior bone contact region, said second bone contact region being higher in an axial direction than said first bone contact region, wherein a transition from said first bone contact region to said second bone contact region has a stepped form including at least two steps, upper contact surfaces of each of said steps being arranged to provide non-migratory support against loading in a primary load-bearing direction, said stepped form defining an effective lordosis plane inclined relative to said primary load-bearing direction, and wherein said upper fixation surface has a generally concave form in a lateral-lateral direction, and wherein said upper fixation surface further features a press-fit anchoring projection, said press-fit anchoring projection having an axial dimension smaller than both its anterior-posterior and its lateral-lateral dimensions, and being formed with two opposing faces inclined to provide a wedge angle of between 1 degree and 30 degrees.

2. The intervertebral, implant of claim, 1, wherein adjacent steps of said at least two steps are spaced apart by between 5 percent and 40 percent of a posterior-anterior dimension of said upper fixation surface.

3. The intervertebral implant of claim 1, wherein adjacent steps of said at least two steps are spaced apart by between 7 percent and 15 percent of a posterior-anterior dimension of said upper fixation surface.

4. The intervertebral implant of claim 1, wherein a height of each of said at least two steps is less than a width of contact surfaces on both sides of said step.

5. The intervertebral implant of claim 1, wherein said stepped form further includes at least one projecting ridge each of which extends along, and adjacent to, at least part of a length of a respective one of said steps.

6. The intervertebral implant of claim 5, wherein each of said at least one projecting ridge has a flank surface which runs into a respective one of said steps.

7. The intervertebral implant of claim 5, wherein each of said at least one projecting ridge terminates at end surfaces deployed to inhibit migration of the implant parallel to said steps.

8. The intervertebral implant of claim. 1, wherein said stepped form is located at least in part in a primary load-bearing region extending at least around a major part of a periphery of said upper fixation surface.

9. The intervertebral implant of claim 8, wherein said primary load-bearing region extends inwards at least about 2 millimeters from the periphery of said upper fixation surface.

10. The intervertebral implant of claim 8, wherein the primary load-bearing region extends over substantially the entirety of said upper fixation surface.

11. The intervertebral implant of claim 1, wherein said press-fit anchoring projection is formed with corner regions deployed to provide anchoring against axial rotational migration of the intervertebral implant.

12. The intervertebral implant of claim 1, wherein said implant structure is a rigid spacer providing a second fixation surface for fixation to the other of the vertebral endplates, said second fixation surface being in fixed spatial relation to said first fixation surface.

13. The intervertebral implant of claim 1, wherein said implant structure is a total disc replacement, and wherein said at least one implant element is implemented as at least two implant elements interconnected by a joint arrangement.

14. The intervertebral implant of claim 13, wherein said joint arrangement includes a ball-and-socket joint.

15. The intervertebral implant of claim 13, wherein said joint arrangement includes a flexible cushion.

16. The intervertebral implant of claim 13, wherein said joint arrangement is configured to increase an intervertebral spacing between the superior and inferior vertebral bodies as a smooth function of angular displacement from a neutral position over at least part of a range of motion in each of at least two independent directions of angular displacement.

* * * * *